US011484586B2

(12) United States Patent
Schnell et al.

(10) Patent No.: US 11,484,586 B2
(45) Date of Patent: Nov. 1, 2022

(54) COMPOSITIONS AND ADMINISTRATION OF CHIMERIC GLYCOPROTEIN LYSSAVIRUS VACCINES FOR COVERAGE AGAINST RABIES

(71) Applicants: Thomas Jefferson University, Philadelphia, PA (US); ICAHN School of Medicine at Mount Sinai, New York, NY (US)

(72) Inventors: Matthias Schnell, Harleysville, PA (US); Christine Rettew Fisher, Philadelphia, PA (US); Christoph Wirblich, Philadelphia, PA (US); Gene Tan, La Jolla, CA (US)

(73) Assignees: Thomas Jefferson University, Philadelphia, PA (US); ICAHN School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 16/623,026

(22) PCT Filed: Jun. 13, 2018

(86) PCT No.: PCT/US2018/137322
§ 371 (c)(1),
(2) Date: Dec. 16, 2019

(87) PCT Pub. No.: WO2018/231974
PCT Pub. Date: Dec. 20, 2018

(65) Prior Publication Data
US 2021/0145959 A1    May 20, 2021

Related U.S. Application Data

(60) Provisional application No. 62/519,625, filed on Jun. 14, 2017.

(51) Int. Cl.
*A61K 39/12* (2006.01)
*C12N 15/86* (2006.01)
*A61K 39/00* (2006.01)

(52) U.S. Cl.
CPC .............. *A61K 39/12* (2013.01); *C12N 15/86* (2013.01); *A61K 2039/5252* (2013.01); *A61K 2039/53* (2013.01); *C12N 2760/20134* (2013.01)

(58) Field of Classification Search
None
See application file for complete search history.

(56) References Cited

U.S. PATENT DOCUMENTS

2008/0206282 A1    8/2008  Jacob et al.
2008/0311147 A1   12/2008  Schnell et al.
2016/0114026 A1    4/2016  Wu et al.
2016/0257719 A1    9/2016  Messer et al.

OTHER PUBLICATIONS

Fisher et al., Cell Reports, Jul. 21, 2020, 32, 107920, pp. 1-13 and e1-e7. (Year: 2020).*
Bahloul, C., et al., "DNA-based immunization for exploring the enlargement of immunological cross-reactivity against the lyssaviruses", Vaccine, vol. 16, No. 4, pp. 417-425, 1998.
Banyard, A.C., et al., "Lyssaviruses and Bats: Emergence and Zoonotic Threat", Viruses, vol. 6, No. 8, pp. 2974-2990, 2014.
Blaney, J.E., et al., "Antibody Quality and Protection from Lethal Ebola Virus Challenge in Nonhuman Primates Immunized with Rabies Virus Based Bivalent Vaccine", PLOS Pathogens, vol. 9, No. 5, Article No. e1003389, 13 pages, 2013.
Botvinkin, A.D., et al., "Novel Lyssaviruses Isolated from Bats in Russia", Emerging Infectious Diseases, vol. 9, No. 12, pp. 1623-1625, 2003.
Ceballos, N.A., et al., "Novel Lyssavirus in Bat, Spain", Emerging Infectious Diseases, vol. 19, No. 5, pp. 793-795, 2013.
Cenna, J., et al., "Immune Modulating Effect by a Phosphoprotein-deleted Rabies Virus Vaccine Vector Expressing Two Copies of the Rabies Virus Glycoprotein Gene", Vaccine, vol. 26, No. 50, pp. 6405-6414, 2008.
Coertse, J., et al., "New isolations of the rabies-related Mokola virus from South Africa", BMC Veterinary Research, vol. 13, No. 1, pp. 37-44, 2017.
De Benedictis, P., et al., "Development of broad-spectrum human monoclonal antibodies for rabies post-exposure prophylaxis", EMBO Molecular Medicine, vol. 8, No. 4, Article No. e201505986, pp. 407-421, 2016.
Evans, J.S., et al., "Rabies virus vaccines: Is there a need for a pan-lyssavirus vaccine?", Vaccine, vol. 30, No. 52, pp. 7447-7454, 2012.
Genz, B., et al., Chimeric rabies viruses for trans-species comparison of lyssavirus glycoprotein ectodomain functions in virus replication and pathogenesis, Berliner und Münchener Tierärztliche Wochenschrift, vol. 125, Nos. 5-6, pp. 219-227, 2012.
Gomme, E.A., et al., "Characterization of a Single-Cycle Rabies Virus-Based Vaccine Vector", Journal of Virology, vol. 84, No. 6, pp. 2820-2831, 2010.
Gunawardena, P.S., et al., "Lyssavirus in Indian Flying Foxes, Sri Lanka", Emerging Infectious Diseases, vol. 22, No. 8, pp. 1456-1459, 2016.

(Continued)

*Primary Examiner* — Stacy B Chen
(74) *Attorney, Agent, or Firm* — Riverside Law LLP

(57) ABSTRACT

The present disclosure is directed towards chimeric glycoproteins wherein the clip region, a core region, a flap region, and a transmembrane and cytoplasmic domain are defined by starting from the amino terminus of the protein, these domains are comprised of the following amino acid residue ranges: clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain; and wherein the clip, core, flap, transmembrane, and cytoplasmic domain comprise a chimeric combination of at least two lyssavirus, wherein the chimeric glycoprotein is advantageously inserted into a rabies-based vaccine vector.

10 Claims, 17 Drawing Sheets

(56) References Cited

OTHER PUBLICATIONS

Hanlon, C.A., et al., "Efficacy of rabies biologics against new lyssaviruses from Eurasia", Virus Research, vol. 111, No. 1, pp. 44-54, 2005.

Hu, S-C, et al., "Lyssavirus in Japanese Pipistrelle, Taiwan", Emerging Infectious Diseases, vol. 24, No. 4, pp. 782-785, 2018.

Hudacek, A.W., et al., "Recombinant rabies virus particls presenting botulinum neurotoxin antigens elicit a protective humoral response in vivo", Molecular Therapy Methods & Clinical Development, vol. 1, 14046, 9 pages, 2014.

Jallet, C., et al., "Chimeric Lyssavirus Glycoproteins with Increased Immunological Potential", Journal of Virology, vol. 73, No. 1, pp. 225-233, 1999.

Johnson, N., et al., "The immune response to rabies virus infection and vaccination", Vaccine, vol. 28, No. 23, pp. 3896-3901, 2010.

Kurup, D., et al., Rhabdovirus-Based Vaccine Platforms against Henipaviruses, Journal of Virology, vol. 89, No. 1, pp. 144-154, 2015.

Liu, Y., et al., "Evaluation of Rabies Biologics against Irkut Virus Isolated in China", Journal of Clinical Microbiology, vol. 51, No. 11, pp. 3499-3504, 2013.

McGettigan, J.P., et al., "Expression and Immunogenicity of Human Immunodeficiency Virus Type 1 Gag Expressed by a Replication-Competent Rhabdovirus-Based Vaccine Vector", Journal of Virology, vol. 75, No. 18, pp. 8724-8732, 2001.

McGettigan, J.P., et al., "Second-Generation Rabies Virus-Based Vaccine Vectors Expressing Human Immunodeficiency Virus Type 1 Gag Have Greatly Reduced Pathogenicity but Are Highly Immunogenic", Journal of Virology, vol. 77, No. 1, pp. 237-244, 2003.

McGettigan, J.P., et al., "Safety and Serological Response to a Matrix Gene-deleted Rabies Virus-based Vaccine Vector in Dogs", Vaccine, vol. 32, No. 15, pp. 1716-1719, 2014.

Mebatsion, T., et al., "Mokola Virus Glycoprotein and Chimeric Proteins Can Replace Rabies Virus Glycoprotein in the Rescue of Infectious Defective Rabies Virus Particles", Journal of Virology, vol. 69, No. 3, pp. 1444-1451, 1995.

Mebatsion, T., "Extensive Attenuation of Rabies Virus by Simultaneously Modifying the Dynein Light Chain Binding Site in the P Protein and Replacing Arg333 in the G Protein", Journal of Virology, vol. 75, No. 23, pp. 11496-11502, 2001.

Moeschler, S., et al., Quantification of Lyssavirus-Neutralizing Antibodies Using Vesicular Stomatitis Virus Pseudotype Particles, Viruses, vol. 8, No. 9, pp. 254-267, 2016.

Morimoto, K., et al., "High level expression of a human rabies virus-neutralizing monoclonal antibody by a rhabdovirus-based vector", Journal of Immunological Methods, vol. 252, Nos. 1-2, pp. 199-206, 2001.

Nokireki, T., et al., "Tentative novel lyssavirus in a bat in Finland", Transboundary and Emerging Diseases, vol. 65, No. 3, pp. 593-596, 2018.

Papaneri, A.B., et al., "Alanine scanning of the rabies virus glycoprotein antigenic site III using recombinant rabies virus: Implication for post-exposure treatment", Vaccine, vol. 31, No. 49, pp. 5897-5902, 2013.

Papaneri, A.B., "Controlled viral glycoprotein expression as a safety feature in a bivalent rabies-ebola vaccine", Virus Research, vol. 197, pp. 54-58, 2015.

Reardon, T.R., et al., "Rabies Virus CVS-N2cΔG Strain Enhances Retrograde Synaptic Transfer and Neuronal Viability", Neuron, vol. 89, No. 4, pp. 711-724, 2016.

Roche, S., et al., "Crystal Structure of the Low-pH Form of the Vesicular Stomatitis Virus Glycoprotein G", Science, vol. 313, No. 5784, pp. 187-191, 2006.

Roche, S., et al., "Structure of the prefusion form of the vesicular stomatitis virus glycoprotein G", Science, vol. 315, No. 5813, pp. 843-848, 2007.

Sabeta, C.T., et al., "Mokola Virus in Domestic Mammals, South Africa", Emerging Infectious Diseases, vol. 13, No. 9, pp. 1371-1373, 2007.

Schnell, M.J., et al., "The cell biology of rabies virus: using stealth to reach the brain", Nature Reviews Microbiology, vol. 8, No. 1, pp. 51-61, 2010.

Smith, J.S., et al., "A rapid reproducible test for determining rabies neutralizing antibody", Bull. World Health Organ., vol. 48, No. 5, pp. 535-541, 1973.

Wei, J-C., et al., "Design and evaluation of a multi-epitope peptide against Japanese encephalitis virus infection in BALB/c mice", Biochemical Biophysical Research Communications, vol. 396, No. 4, pp. 787-792, 2010.

Willet, M., et al., "Preclinical Development of Inactivated Rabies Virus-Based Polyvalent Vaccine Against Rabies and Filoviruses", Journal of Infectious Diseases, vol. 212, Supplement 2, pp. S414-S424, 2015.

Xu, H., et al., "Evaluation of a Novel Chimeric B Cell Epitope-Based Vaccine against Mastitis Induced by Either *Streptococcus agalactiae* or *Staphylococcus aureus* in Mice", Clinical and Vaccine Immunology, vol. 18, No. 6, pp. 893-900, 2011.

Zhou, W.Y., et al., "Therapeutic efficacy of a multi-epitope vaccine against Helicobacter pylori infection in BALB/c mice model", Vaccine, vol. 27, No. 36, pp. 5013-5019, 2009.

International Search Report and Written Opinion in International Application No. PCT/US2018/037322, International Searching Authority United States, dated Aug. 30, 2018.

\* cited by examiner

FIG. 1

RABV G

N —[ Clip | Core | Flap | TM & cytoplasmic domain ]— C

Site IIb, Site IIa, Site I, Site IV, Site III, Site a

Chimera1 G

N —[ Clip | Core | Flap | TM & cytoplasmic domain ]— C

Chimera2 G

N —[ Clip | Core | Flap | TM & cytoplasmic domain ]— C

RABV G

FIG. 7D

MOKV G

Chimera 2 G

Immunize (10 μg i.m.)  Challenge (5E5 ffu i.n.)

Day 0   7   14   21   28   35   56   84/NEC

FIG. 8B

|   | Vaccine | Challenge virus |
|---|---------|-----------------|
| Group A | Mock vaccination (PBS) | 5 x $10^5$ ffu live SPBN |
| Group B | Mock vaccination (PBS) | 5 x $10^5$ ffu live BNSPΔG-coMOKVG |
| Group C | 10 μg inactivated BNSPΔG-Chimera1 | 5 x $10^5$ ffu live SPBN |
| Group D | 10 μg inactivated BNSPΔG-Chimera1 | 5 x $10^5$ ffu live BNSPΔG-coMOKVG |

FIG. 8C

RABV CVS11 neutralization

COMPOSITIONS AND ADMINISTRATION OF CHIMERIC GLYCOPROTEIN LYSSAVIRUS VACCINES FOR COVERAGE AGAINST RABIES

PRIORITY CLAIM

This application claims the benefit of U.S. Provisional Application No. 62/519,625, filed Jun. 14, 2017, which is hereby incorporated by reference in its entirety.

GOVERNMENT SUPPORT

This invention was made with government support under AI128175 awarded by the National Institutes of Health. The government has certain rights in the invention.

FIELD OF INVENTION

The present invention is generally related to the composition of a chimeric glycoprotein vaccine as well as methods of administration of this vaccine to protect from a spectrum of rabies-causing lyssaviruses not covered by current vaccines.

BACKGROUND OF INVENTION

Rabies disease is a significant medical issue globally, causing an estimated 55,000 deaths annually.[1] Rabies virus infects the central nervous system and is transmitted through the saliva of infected animals. Although it is fully treatable if the vaccine is administered promptly and correctly, it is almost always fatal if the symptoms appear before proper treatment is given. As such, prompt treatment for rabies is crucial to avoid fatalities.

17 rabies-related viruses, categorized as lyssaviruses, are able to cause rabies disease, and seven lyssaviruses have been implicated in human fatalities to date. Gunawardena, Panduka S., et al. "Lyssavirus in Indian Flying Foxes, Sri Lanka." *Emerging infectious diseases* 22.8 (2016): 1456; Ceballos, Nidia Aréehiga, et al. "Novel lyssavirus in bat, Spain." *Emerging infections diseases* 19.5 (2013): 793. In addition, the discovery of new rabies-related viruses continues as surveillance efforts improves. Nokireki, T., et al. "Tentative novel lyssavirus in a bat in Finland." *Transboundary and emerging diseases* 65.3 (2018): 593-596.Hu, Shu-Chia, et al. "Lyssavirus in Japanese Pipistrelle, Taiwan." *Emerging infectious diseases* 24.4 (2018): 782, Symptoms are indistinguishable between lyssavirus infections. Lyssaviruses fall into one of three phylogroups based on genetic differences between them and antiserum cross-reactivity.[2] However, current rabies vaccines, including the Human Diploid Cell Vaccine (Imovax) and Purified Chick Embryo Cell Vaccine (RabAvert), only protect against classical rabies virus (RABV) and some closely-related species, which fall under Phylogroup I. Wang Y, Zhang J, Hu R. Evaluation of rabies biologics against Irkut virus isolated in China. J Clin Microbiol. 2013; 51(11):3499-504. doi: 10.1128/JCM.01565-13. PubMed PMID: 23946522; PMCID: PMC3889725. These vaccines fail to protect against more distant, emerging lyssaviruses which fall under Phylogroup II and III.[3,4] This failure of protection is especially seen in cases of domestic pets succumbing to rabies disease cause by a non-RABV lyssavirus, despite being vaccinated for RABV. Coertse J, Markotter W, le Roux K, Stewart D, Sabeta C T, Nel L H. New isolations of the rabies-related Mokola virus from South Africa. BMC veterinary research. 2017; 13(1):37. Epub 2017/02/02. doi: 10.1186/s12917-017-0948-0. PubMed PMID: 28143485; PMCID: PMC5282659; Sabeta C T. Mokola Virus in Domestic Mammals, South Africa-Volume 13, Number 9—September 2007-Emerging Infectious Disease journal-CDC$I_2$007. Without a more comprehensive vaccine, proper treatment of rabies is not possible.

In developing more broadly protective vaccines, there has been a shift towards developing "epitope-based vaccines", as these vaccines are safer, more potent, and have a wider breadth.[5,6,7] One well-established technique to develop an epitope-based vaccine is to create a chimeric protein antigen. Under such an approach, a viral glycoprotein (G) is combined with another viral G to form a chimera. This chimera would elicit an antibody response from either virus upon exposure, thus broadening the scope of protection provided by a single vaccine.

A few precedents in chimeric rabies vaccines have already been set through the use of RABV and non-RABV lyssavirus Gs.[8,9,10] These studies lay important groundwork for understanding the possibilities and limitations in engineering lyssavirus Gs. Prior work in the field has led to the creation of RABV G/MOKV G chimeric glycoproteins through the exchange of large domains and short regions, but many of these chimeras were not functional.[11] In another attempt, DNA immunization of mice using chimeric Gs demonstrated protection against both RABV and MOKV challenge, however the use of DNA immunization limits the translatability of these studies into vaccine potential.[12,13]

More virus isolates have been collected and analyzed over the past decade, expanding knowledge of genetic and antigenic relationships among lyssaviruses. Furthermore, new structural information about related rhabdoviruses has since been solved.[14,15] Taken together, there is a need to revisit chimeric constructions as vaccine potentials to pave the way for a novel pan-lyssavirus vaccine. Herein, we have developed new chimeric Gs that have overcome the non-functional status of the prior chimeras and developed a new vaccine that generates a more robust response to a larger class of lyssaviruses.

SUMMARY OF INVENTION

The present invention is directed to chimeric lyssavirus glycoproteins (Gs) and methods of administration to confer broader protection against rabies and other lyssaviruses than is currently available.

In preferred embodiments, herein is described a chimeric lyssavirus glycoproteins and methods of administration to confer broader protection against rabies and other lyssaviruses than is currently available. In certain embodiments, the glycoprotein is constructed from a specific combination of glycoproteins into a single chimera, which is then inserted into a vaccine vector. In certain embodiments, the vaccine vector is rabies-based. In certain further embodiments, these chimeric glycoprotein vectors are inactivated and administered as a vaccine. In certain further embodiments, the vaccine is administered via a specific dosing regimen similar to those used by current vaccines. In a further embodiment, multiple chimeras originating from different glycoprotein combinations may be combined into a single "cocktail" vaccine for broad protection against lyssaviruses.

In a preferred embodiment of the present invention, a chimeric G comprises a clip, flap, transmembrane, cytoplasmic domain, and a core, wherein the clip, flap, transmembrane, and cytoplasmic domain of the chimera are from a RABV glycoprotein, while the core of the chimera is from a MOKV glycoprotein. In another preferred embodiment, the clip and flap are from a MOKV glycoprotein, while the core, transmembrane and cytoplasmic domain are from the RABV glycoprotein. In a preferred embodiment, the constructed chimeric glycoproteins are inserted between the nucleoprotein and phosphoprotein into a rabies-based vaccine vector missing a glycoprotein.

In a further embodiment, the chimeric glycoproteins in a vaccine vector are inactivated with either beta-propiolactone (BPL), formalin, irradiation, or another reasonable method and used in a vaccine which can be administered intramuscularly. In further embodiments the vaccine is administered following a dosing regimen of 3 doses over 4 weeks (for pre-exposure prevention of rabies infection) or 4-5 doses over 4 weeks (for post-exposure active immunity). In certain embodiments the chimeric glycoprotein may comprise a combination of any two of RABV, IRKV, MOKV and LBV glycoproteins, or may comprise a combination of any two glycoproteins of the 17 currently known lyssavirus species. Preferably, the two glycoproteins are from different phylogroups. In a further embodiment, multiple constructed chimeric glycoproteins originating from different glycoprotein combinations may be combined into a single "cocktail" vaccine for similarly broad protection against lyssaviruses, wherein said cocktail comprises at least two different chimeric glycoproteins corresponding to at least 3 of the currently known lyssavirus species.

A preferred embodiment is directed towards a chimeric lyssavirus glycoprotein comprising components of both RABV and MOKV glycoproteins within a clip region, a core region, a flap region, and a transmembrane and cytoplasmic domain.

In a further embodiment, the chimeric glycoprotein wherein the clip region is from a RABV glycoprotein; wherein the core region is from a MOKV glycoprotein; wherein the flap region is from a RABV glycoprotein; and wherein the transmembrane and cytoplasmic domain are from a RABV glycoprotein.

In a further embodiment, the chimeric glycoprotein wherein the glycoprotein is inserted into the BNSPΔG virus vector between the nucleoprotein and the phosphoprotein.

In a further embodiment, the chimeric glycoprotein wherein the glycoprotein inserted into the BNSPΔG vector is inactivated and provided in a vaccine.

In a further embodiment, the chimeric glycoprotein wherein the inactivation is generated by contact with beta-propiolactone (BPL), formalin, irradiation, or another reasonable method.

In a further embodiment, the chimeric glycoprotein, wherein the core region is from a RABV glycoprotein; wherein the flap region is from a MOKV glycoprotein; and wherein the transmembrane and cytoplasmic domain are from a RABV glycoprotein.

In a further embodiment, the chimeric glycoprotein, wherein the glycoprotein is inserted into the BNSPΔG virus vector between the nucleoprotein and the phosphoprotein.

In a further embodiment, the chimeric glycoprotein, wherein the glycoprotein inserted into the BNSPΔG vector is inactivated and provided in a vaccine.

In a further embodiment, the chimeric glycoprotein, wherein the clip region, a core region, a flap region, and a transmembrane and cytoplasmic domain are defined by: starting from the amino terminus of the protein, these domains are comprised of the following amino acid residue ranges: clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain.

A preferred embodiment is directed towards a method of conferring broad immunity to lyssaviruses comprising intramuscular administration of a vaccine containing inactivated chimeric glycoprotein viruses, wherein said inactivated chimeric glycoprotein viruses comprise components of both RABV and MOKV glycoproteins within a clip region, a core region, a flap region, and a transmembrane and cytoplasmic domain.

In a further preferred embodiment, the method wherein the vaccine is administered as at least 3 doses over 4 weeks, or wherein the vaccine is administered as at least 4 over 4 weeks.

In a further preferred embodiment, the method wherein the clip, flap, transmembrane, and cytoplasmic domain regions are from a RABV glycoprotein; wherein the core region is from a MOKV glycoprotein.

In a further preferred embodiment, the method wherein the glycoprotein is inserted into the BNSPΔG virus vector between the nucleoprotein and the phosphoprotein.

In a further preferred embodiment, the method wherein the glycoprotein inserted into the BNSPΔG vector is inactivated with beta-propiolactone (BPL), formalin, irradiation, or another reasonable method.

In a further preferred embodiment, the method wherein the clip, flap, transmembrane, and cytoplasmic domain is from a MOKV glycoprotein; and wherein the core region is from a RABV glycoprotein.

In a further preferred embodiment, the method wherein the glycoprotein is inserted into the BNSPΔG virus vector. In a certain embodiment, wherein the glycoprotein inserted into the BNSPΔG vector is inactivated and provided in a vaccine.

In a further preferred embodiment, the method wherein the clip region, core region, flap region, transmembrane, and cytoplasmic domain are defined by starting from the amino terminus of the protein, and are comprised of the following amino acid residue ranges: clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain.

A further embodiment is directed towards a chimeric lyssavirus glycoprotein comprising a combination of any two of RABV, IRKV, MOKV, and LBV glycoproteins within a clip region, a core region, a flap region, and a transmembrane and cytoplasmic domain.

In a further preferred embodiment, the chimeric lyssavirus glycoprotein, wherein the glycoprotein is inserted into the BNSPΔG virus vector between the nucleoprotein and the phosphoprotein.

In a further preferred embodiment, the chimeric lyssavirus glycoprotein, wherein the glycoprotein inserted into the BNSPΔG vector is inactivated and provided in a vaccine.

A further embodiment is directed towards a chimeric lyssavirus glycoprotein comprising a combination of any two of RABV, ARAV, KHUV, BBLV, EBLV-2, ABLY, IRKV, EBLV-1, DUVV, MOKV, SHIBV, LBV, WCBV, IKOV, and LLEBV glycoproteins within a clip region, a core region, a flap region, and a transmembrane and cytoplasmic domain.

A further preferred embodiment wherein the chimeric glycoprotein is inserted into the BNSPΔG virus vector between the nucleoprotein and the phosphoprotein. Preferably, in a preferred embodiment, wherein the glycoprotein inserted into the BNSPΔG vector is inactivated and provided in a vaccine.

A further preferred embodiment wherein the chimeric glycoprotein wherein multiple chimeras originating from different glycoprotein combinations are inserted into the BNSPΔG vector, inactivated, and provided in a vaccine.

A further embodiment is directed towards a chimeric glycoprotein of any of the preceding claims, wherein the glycoproteins contain a clip, core, flap, and a transmembrane and cytoplasmic domain, wherein the glycoprotein present in the clip and flap region is the same and wherein the glycoprotein in the core region is different than the glycoprotein in the clip and flap region. Preferably, wherein the glycoprotein of the transmembrane and cytoplasmic domain is the same as the glycoprotein in the core region. In other embodiments, wherein the glycoprotein of the transmembrane and cytoplasmic domain is the same as the glycoprotein in the clip and flap region.

A preferred embodiment is a chimeric G, comprising a clip, core, flap, and a transmembrane and cytoplasmic domain of at least two different lyssaviruses, administered to a patient in its nucleic acid form.

A preferred embodiment is a BNSPΔG viral vector comprising a clip, core, flap, and a transmembrane and cytoplasmic domain of at least two different lyssaviruses, administered as a vaccine, in its nucleic acid (RNA or DNA) form.

Formulation of a vaccine or medicament comprising the chimeric glycoprotein of any one of the proceeding claims.

Use of a glycoprotein of any one of the proceeding claims for formulating a vaccine or medicament. In preferred embodiments, the vaccine or medicament can be applied before or after contact with a rabies virus and inoculated to a mammal to prevent the formation of rabies virus.

BRIEF DESCRIPTION OF THE DRAWINGS

FIG. 1 Phylogenetic analysis of lyssaviruses with categorizations into Phylogroup I, II, and III. Asterisks represent species which have so far caused human fatalities.

FIG. 4 Structure of Chimeras 1 and 2 within the clip, core, flap, transmembrane and cytoplasmic domain.

FIG. 5 Immunofluorescence confirmation of chimeric G expression showing response to both polyclonal sera by chimeric Gs but response to only one polyclonal serum by wild type Gs.

FIGS. 7A-7G depict a series of structural protein models of RABV G, MOKV G, chimera1 and chimera2, noting structural features (the "clip", "core", and "flap") utilized to design the chimeric Gs.

FIGS. 8A, 8B, and 8C depict an immunization strategy, weight change data, and overall survival from an experiment in which mice were vaccinated and challenged. The chimeric G vaccine completely protected against disease. FIG. 8A specifically depicts how 9/10 mock-vaccinated mice (Groups A and B) succumbed to RABV (Group A, challenged with live SPBN) and MOKV (Group B, challenged with live BNSPΔG-coMOKVG), but all 10 mice immunized with BNSPΔG-chimera1 survived challenge with both live viruses. FIG. 8B depicts the experimental timeline: mice were immunized three times at days 0, 7, and 28, then challenged on day 56. The experiment concluded on day 84. FIG. 8C depicts the exact vaccine and challenge virus given to each group, and the amounts.

FIGS. 9A and 9B depict that chimeric G vaccine elicits high titers of neutralizing antibodies against both RABV and MOKV. FIG. 9A depicts RABV neutralizing titers determined by the RFFIT assay, while FIG. 9B depicts MOKVG neutralizing titers determined by a pseudotype neutralization assay.

DETAILED DESCRIPTION OF THE EMBODIMENTS

Figure 2:
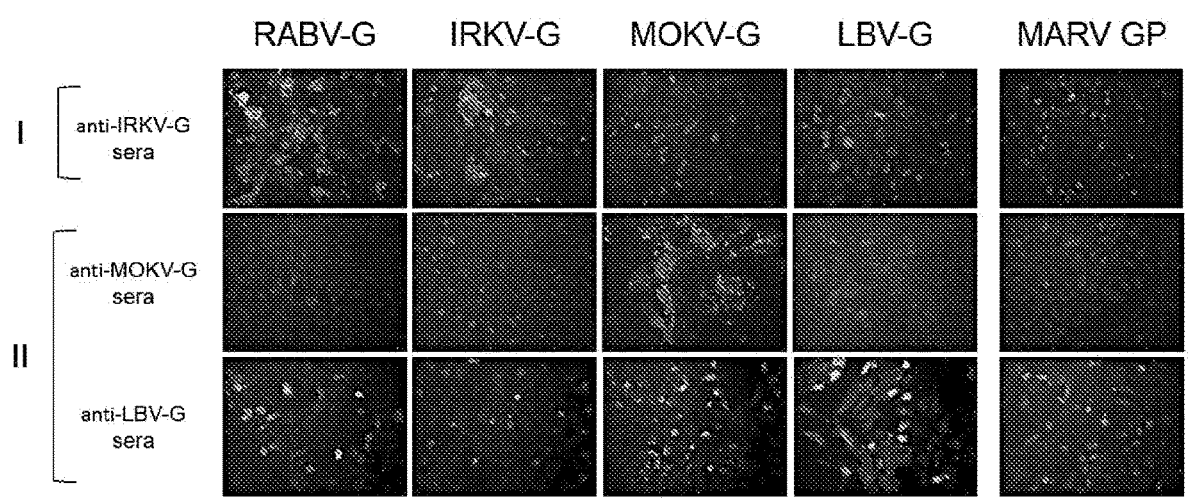
FIG. 2 Immunofluorescence data shows reactivity in Phylogroup I Gs to anti-Phylogroup I sera, but little to no reactivity in other Phylogroups (and vice versa).

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "ABLV" refers to Australian bat lyssavirus.

As used herein, the term "ARAV" refers to Aravan virus.

As used herein, the term "BBLV" refers to Bokeloh bat lyssavirus.

As used herein, the term "BNSP" refers to the standard parent viral vector.

As used herein, the term "BNSPΔG" refers to the standard parent viral vector with RABV G deleted.

As used herein, the term "BPL" refers to β-propriolactone.

As used herein, the term "co" refers to codon optimized.

As used herein, the term "DUVV" refers to Duvenhage virus.

As used herein, the term "EBLV-1" refers to European Bat lyssavirus 1.

As used herein, the term "EBLV-2" refers to European Bat lyssavirus 2.

As used herein, the term "G" refers to glycoprotein.

As used herein, the term "KHUV" refers to Khuj and virus.

As used herein, the term "HDCV" refers to Human Diploid Cell Vaccine.

As used herein, the term "IF" refers to immunofluorescence.

As used herein, the term "IKOV" refers to Ikoma lyssavirus.

As used herein, the term "IRKV" refers to Irkut virus.

As used herein, the term "LBV" refers to Lagos bat virus.

As used herein, the term "LLEBV" refers to Lleida bat virus.

As used herein, the term "MARV" refers to Marburg virus.

As used herein, the term "MOKV" refers to Mokola virus.

As used herein, the term "N" refers to nucleoprotein.

As used herein, the term "P" refers to phosphoprotein.

As used herein, the term "PCECV" refers to Purified Chick Embryo Cell Vaccine.

As used herein, the term "RABV" refers to classical rabies virus.

As used herein, the term "SHIBV" refers to Shimoni bat virus.

As used herein, the term "TM" refers to transmembrane.

As used herein, the term "WCBV" virus refers to West Caucasian bat virus.

As used herein, the term "WT" refers to wild type.

Rabies vaccines are among the oldest antiviral interventions and effectively present disease when administered correctly. There is thus a misconception that rabies no longer poses a threat to human health. However, rabies is a significant medical issue globally, causing an estimated 55,000 deaths annually.[1] Rabies virus infects the central nervous system and is transmitted through the saliva of infected animals. Although it is fully treatable if the vaccine is administered promptly and correctly, rabies encephalitis is considered the most assuredly lethal viral infection known to mankind when no intervention is applied. As such, prompt treatment for rabies is crucial to avoid fatalities.

There are currently seventeen categorized lyssaviruses able to cause rabies. Of these seventeen, seven lyssaviruses have been confirmed as implicated in human fatalities to date. In addition, the discovery of new rabies-related viruses continues as surveillance efforts improves. Symptoms are indistinguishable between lyssavirus infections, and at present, the culpable species can only be confirmed in postmortem analysis. For this reason, the threat of infection with RABV related lyssaviruses is likely underestimated, as differential diagnosis of "rabies" is not always performed, especially in the developing world.

Figure 1:
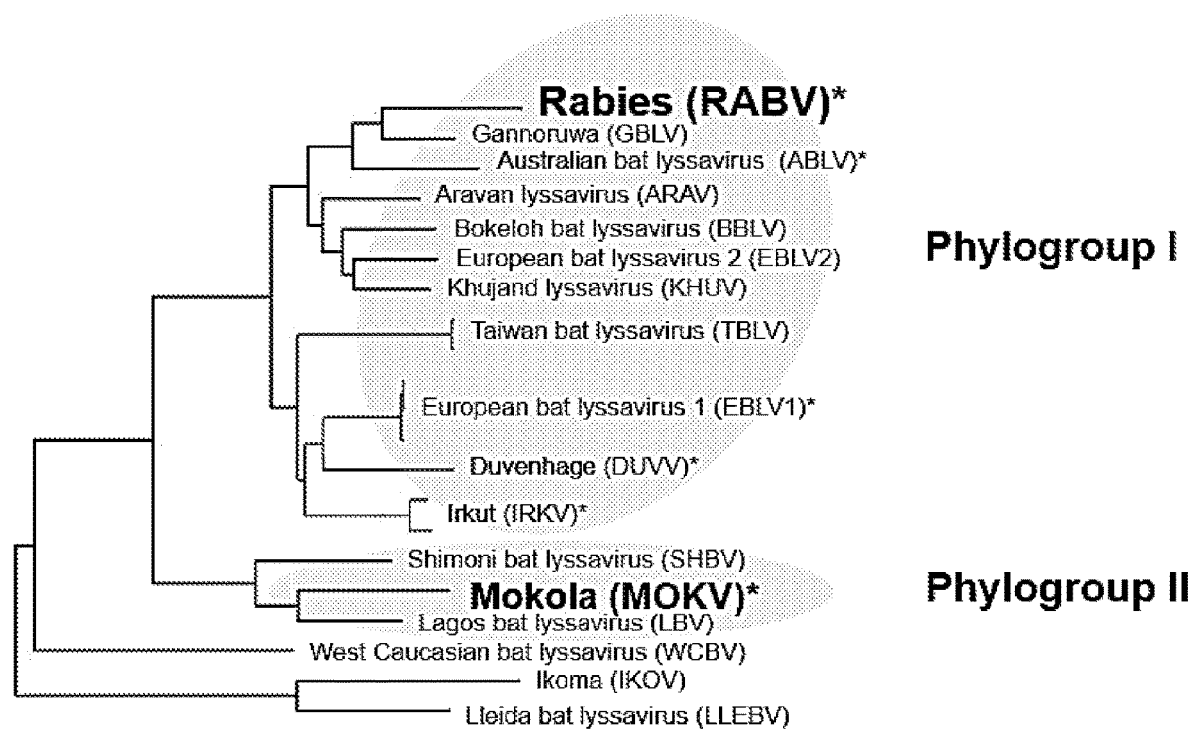

Lyssaviruses fall into one of three phylogroups based on genetic differences between them and antiserum cross-reactivity.[2] The known lyssaviruses include RABV and nine other viruses in Phylogroup I; three lyssaviruses in Phylogroup II; and three highly divergent lyssaviruses loosely grouped into a third phylogroup. FIG. 1 specifically details how the phylogenetic analysis splits lyssaviruses into three distinct groups. Asterisks next to lyssaviruses in the figure indicate species which have been confirmed to have caused human fatalities. The analysis was performed using the maximum-likelihood method. Hu, Shu-Chia, et al. "Lyssavirus in Japanese Pipistrelle, Taiwan." Emerging infectious diseases 24.4 (2018): 782.

However, current rabies vaccines were developed exclusively against RABV, with no regard to other lyssaviruses. Consequently, current vaccines only cross-protect against some closely-related species in Phylogroup I. There is no protection against Phylogroup II and III viruses, and lapses in coverage have even been shown within Phylogroup I.[3,4] Without a more comprehensive vaccine which offers protection across many species, proper treatment of rabies is not possible. FIG. 2 specifically shows the difference in immune serum reactivity against a small panel of lyssavirus Gs. Lyssavirus Gs, including RABV, IRKV, MOKV and LBV, were exposed to specific antibodies in sera. Sera generated against IRKV G only cross-reacts with RABV G, another phylogroup I lyssavirus, while sera generated against phylogroup II lyssaviruses MOKV and LBV have completely different staining patterns. When glycoproteins were exposed to anti-MOKV-G sera, only MOKV-G reacted. When glycoproteins were exposed to anti-LBV-G sera, there was reactivity in LBV-G, limited reactivity in RABV-G and MOKV-G, and no reactivity in IRKV-G. MARV was used as a control, as it is not part of the three phylogroups and would not react to any sera. This data shows that while the current vaccine (represented by anti-IRKV-G sera) protects against Phylogroup I viruses, it has limited to no effect on Phylogroup II and III viruses. The data confirms what is well-established in the field: though lyssaviruses are similar enough to cause the same disease, their Gs are different enough to cause different serum staining profiles. De Benedictis, Paola, et al. "Development of broad-spectrum human monoclonal antibodies for rabies post-exposure prophylaxis." *EMBO molecular medicine* (2016): e201505986. Serum cross-reactivity is important because it is the main correlate of protection in rabies disease. That is, if an individual receives a vaccine and generates a serum immune response, they will be protected. The more broadly a person's serum can cross-react against lyssaviruses, the more likely they will be protected. Thus, a broad vaccine generating cross-reactive sera is necessary.

Despite the clear and apparent need for a broader vaccine, the two vaccines currently licensed in the United States are based on killed rabies virus. HDCV, known as Imovax in the USA, is prepared from the Pitman-Moore strain of rabies grown on MRC-5 human diploid cell culture, concentrated by ultrafiltration, and inactivated with beta-propiolactone. PCECV, also known as RabAvert, is prepared from the fixed rabies virus strain Flury LEP grown in primary cultures of chicken fibroblasts. The virus is inactivated with beta-propiolactone and further processed by zonal centrifugation in a sucrose density gradient. Neither vaccine protects against lyssaviruses outside of Phylogroup I. A more broadly covering vaccine would reduce the number of fatalities both in the US and globally. Furthermore, a complete vaccine, one that protects against lyssaviruses outside of Phylogroup I, would ensure that vaccine results match consumer expectations of full protection against rabies rather than limited viability in present forms.

The present invention is directed towards a chimeric G constructed from components of multiple lyssaviruses. When inserted into a vector, it can be used as a vaccine following a dosing regimen to treat rabies more broadly than current vaccines on the market. In addition, it is faster to grow chimeric Gs, leading to easier and faster manufacturing of vaccines.

A balance of safety and immunogenicity is imperative to the employment of a successful vaccine. Over the past 15 years, the inventors have developed the rabies-based vaccine vector BNSP which is designed to uphold this balance. This vector originates from the validated RABV SAD B19 vaccine strain and has been optimized through the exploration of numerous attenuation methods[9, 16-20] and foreign antigen incorporation, including HIV-1 and Ebolavirus proteins.[9, 21-24] For these reasons, the rabies-based vector is designed specifically for optimal use in a new generation of lyssavirus vaccines.

It is well-established that virus-neutralizing antibodies are most critical for protection against and clearance of RABV.[25] The glycoprotein is the sole protein on the virion surface and is the only target which elicits neutralizing antibodies.[9] Functionally, the glycoprotein engages with host cell receptors, mediates membrane fusion, and is a major determinant of pathogenicity.

In creating our chimeric Gs, we used structural modeling to design proteins with the least disturbance to structure and function. No lyssavirus G structures have yet been solved, so we studied the most closely related viral G, that of Vesicular Stomatitis Virus (VSV). Observations about tertiary amino acid chain interactions suggested that the region closest to the N-terminal domain ("clip") associates closely with a distal portion of the ectodomain ("flap"), but are separated by a large unassociated domain ("core"). We utilize these terms, clip, flap, and core throughout to refer to these domains in the generation of the chimeric Gs. This particular chimeric G was created in the following manner: Starting from the amino terminus of the protein, these domains are comprised of the following amino acid residues: clip, 1 through 50; core, 51 through 278; flap, 279 through 419. The transmembrane domain is comprised of amino acids 460 through 480, and the remaining amino acids 481 through 525 comprise the cytoplasmic domain. The inventors hypothesized that in designing a chimeric G, the clip and flap should come from the same G to preserve perceived native structural and functional integrity, whereas the core can come from the G of another species. These amino acid residues may fall within a range, for example, the clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain.

Figure 7A:
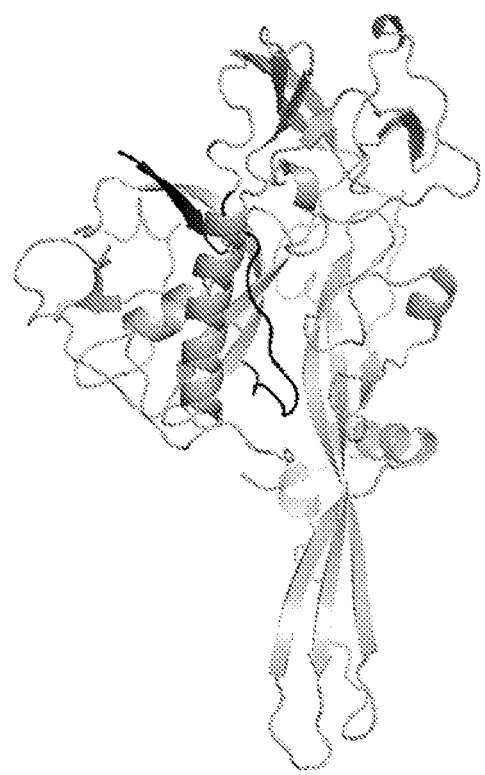
Figure 7B:
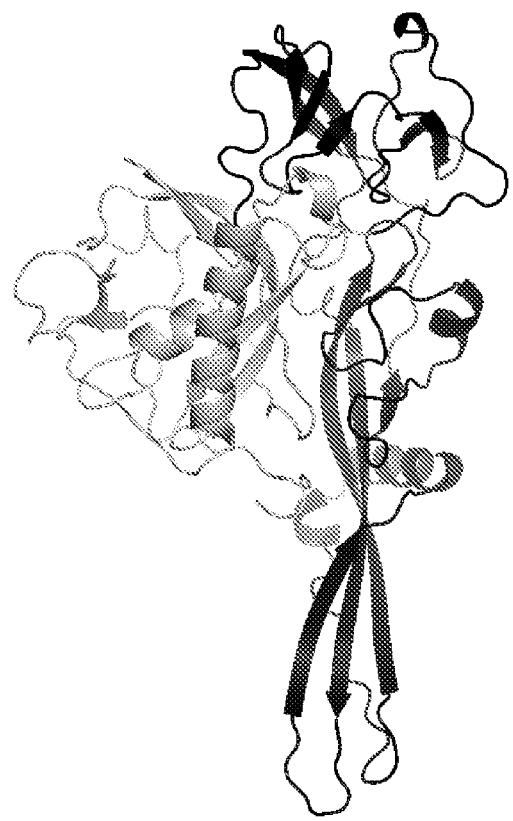
Figure 7C:
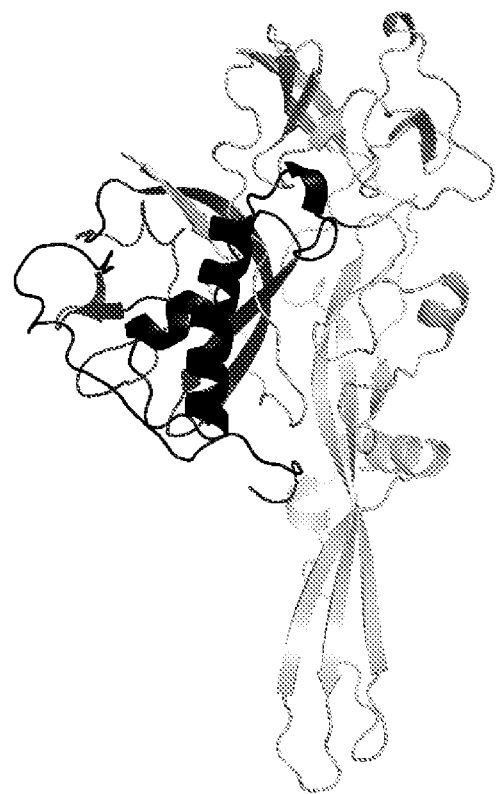
Figure 7D:
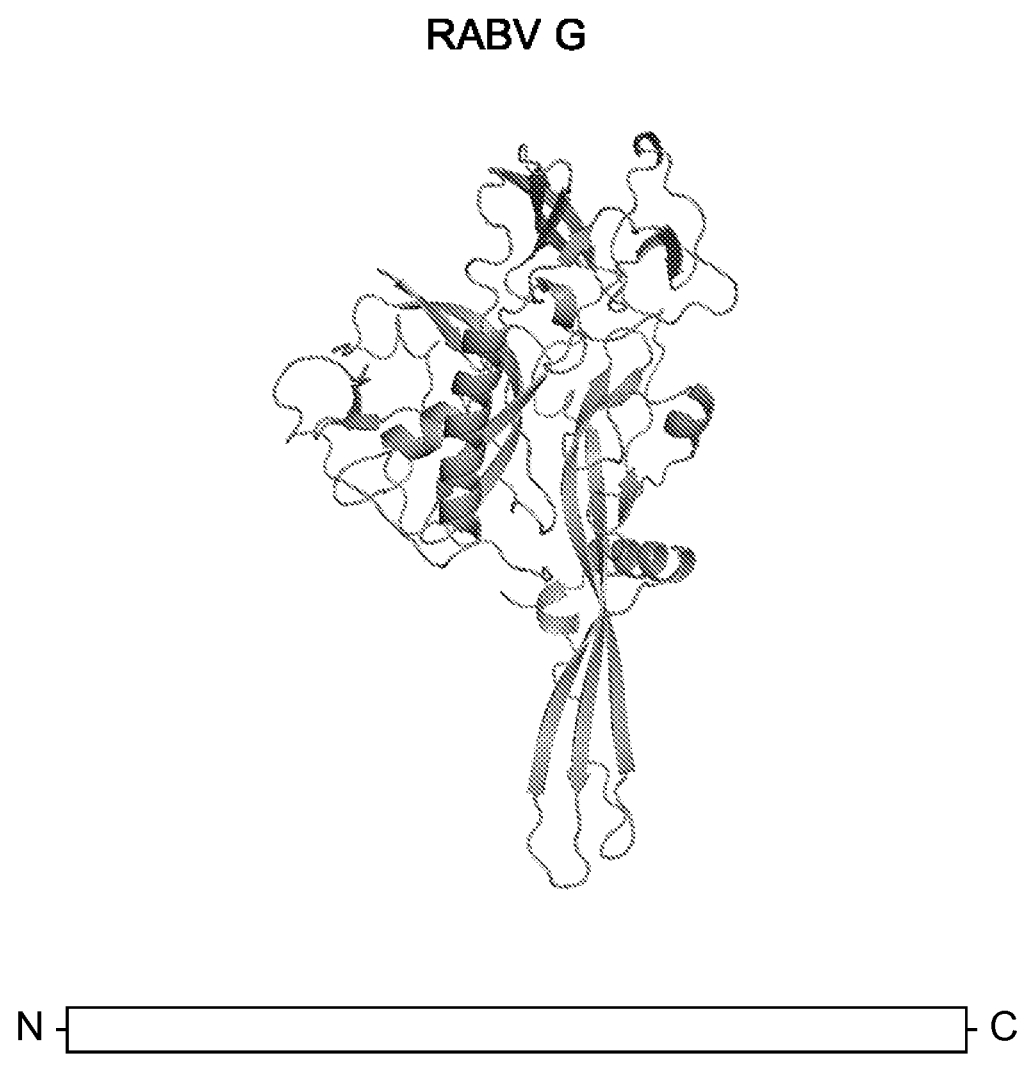
Figure 7E:
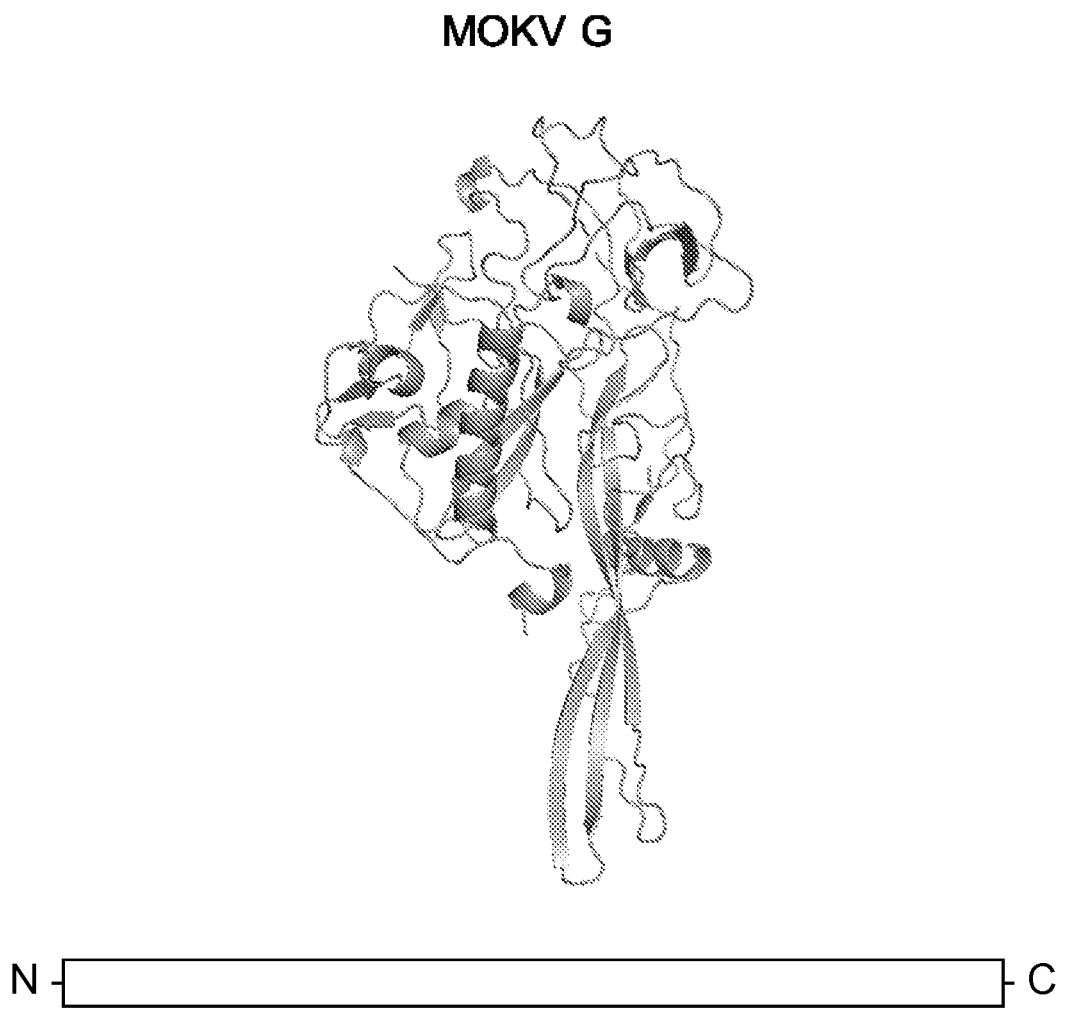
Figure 7F:
Figure 7G:
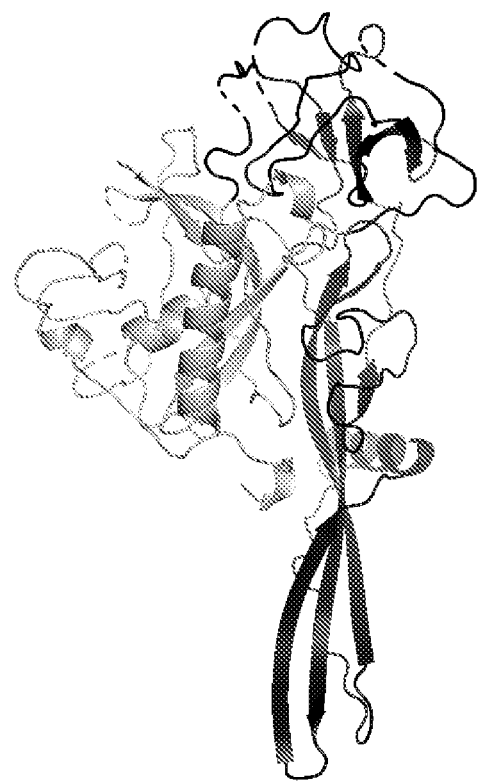
Figure 7G:

FIG. 4 depicts a linear diagram of the wild-type RABV G and chimeric Gs. Chimera 1 consists of a RABV clip, flap, TM & cytoplasmic domain. The core is from a MOKV G. Chimera 2 consists of a MOKV clip and flap, while the core, TM & cytoplasmic domain are from RABV. FIG. 7 depicts a series of structural models of lyssavirus Gs which were used to design the chimeric Gs. First, we highlight the structural domains observed and utilized to design the chimeric Gs: in FIG. 7A, the "clip" is noted in black, in FIG. 7B, the "core" is noted in black, and in FIG. 7C, the "flap" is noted in black. FIGS. 7D and 7E depict wild-type RABV G and MOKV G, respectively. The final two panels depict chimeric Gs: FIG. 7F shows chimera1, in which the "clip" and "flap" (shown in black) are derived from RABV G, and the "core" is derived from MOKV G. FIG. 7G shows chimera2, in which the "core" (shown in black) is derived from RABV G, and the "clip" and "flap" are derived from MOKV G.

Importantly, major antigenic regions, or immune "hot spots", are balanced among portions of the chimeric Gs which come from separate proteins. For example, there are three antigenic regions on the flap (sites a, III, and IV) and two antigenic regions on the core (sites I and II). This balance is necessary to generate equitable immune responses against both component Gs. Since the other proteins in the vaccine are wild-type RABV proteins, the transmembrane (TM) and cytoplasmic domains from RABV G were used in all instances to preserve interactions with the matrix protein.

Chimeric Gs are constructed using InFusion cloning and confirmed via sequencing. Gs were tested for expression and antigenicity by transient transfection in Vero cells. Cells were fixed with paraformaldehyde (pfa) 48 hours post-transfection and stained with monoclonal and polyclonal antibodies. Monoclonal anti-RABV G antibodies stain only one of the chimeric Gs produced, while polyclonal sera stains both. (FIG. 5).

Figure 5:
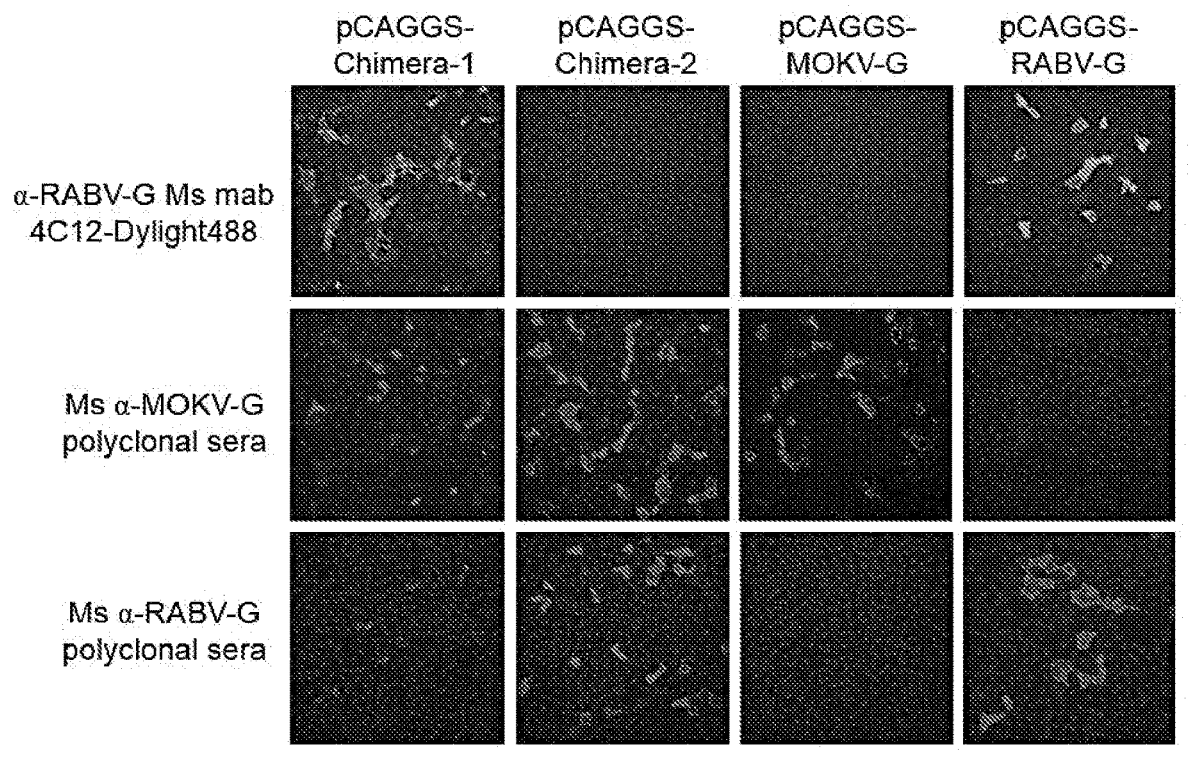

As shown in FIG. 5 the IF data confirms chimeric G cross-reactivity. Cells transiently transfected with expression vectors containing either the chimeric Gs, MOKV-G, or RABV-G are exposed to either monoclonal antibodies or polyclonal sera. When exposed to an anti-RABV-G monoclonal antibody (which has an epitope located in the flap region of RABV G), Chimera 1 reacts, as does the RABV-G.

Chimera 2 (which has a flap region from MOKV G) and MOKV-G do not react. The monoclonal antibody staining confirms that the chimeric Gs were constructed properly. When exposed to anti-MOKV-G polyclonal sera, both chimeras react, as well as the MOKV-G. RABV-G alone does not react. When exposed to anti-RABV-G polyclonal sera, both chimeras react, as well as RABV-G, however MOKV-G does not react. When immunized with a rabies vaccine, an individual develops polyclonal serum response which forms the basis for protection. The positive staining of both chimeras with both anti-RABV G and anti-MOKV G sera demonstrates broadened cross-reactivity.

Figure 3:
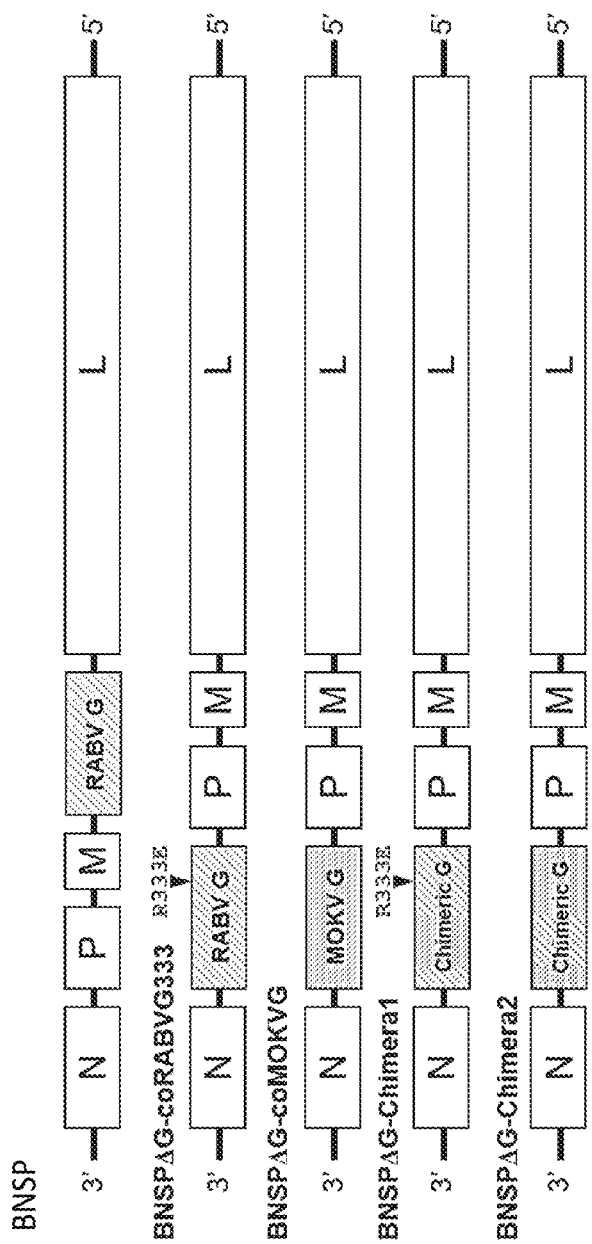
FIG. 3 Diagram demonstrating the process for constructing chimeric Gs, including removing the native G and inserting a codon optimized alternate G between the nucleoprotein and phosphoprotein.

Using standard molecular cloning, chimeric Gs are inserted into the parent vector BNSPΔG between N and P. Indeed, FIG. 3 depicts a diagram depicting the technique for chimeric G vaccine construction. The native G is removed from a BNSP vector, forming a BNSPΔG. From there, a coG is inserted between the N and P. This G can be a standard RABV G, or, in the case of chimeric G construction as we have described herein, can be a chimeric G.

BNSPΔG was selected as it has been shown that MOKVG can rescue infectivity in G-deleted rabies vectors[11] and the same is true for other lyssavirus Gs. In addition, it has been shown that insertion of Gs into the position between the N and P genes yields high levels of protein expression and that the genome tolerates foreign gene insertion in this position without issue.[9, 21] Accordingly, while other positions, outside of the N and P location may be suitable, the increased protein expression in this N and P location is advantageous. Using a well-established reverse genetics approach[23, 27-30] the viruses are recovered by co-transfection of BSR cells with the cloned constructs as well as support plasmids encoding individual viral genes (RABV N, P, L) and a plasmid expressing T7 RNA polymerase.

Chimeric viruses are concentrated and purified over a sucrose cushion and the virus particles are inactivated, in this particular instance, using BPL. Their complete inactivation is confirmed through two rounds of sub-culturing on BSR cells.[23]

Figure 6:
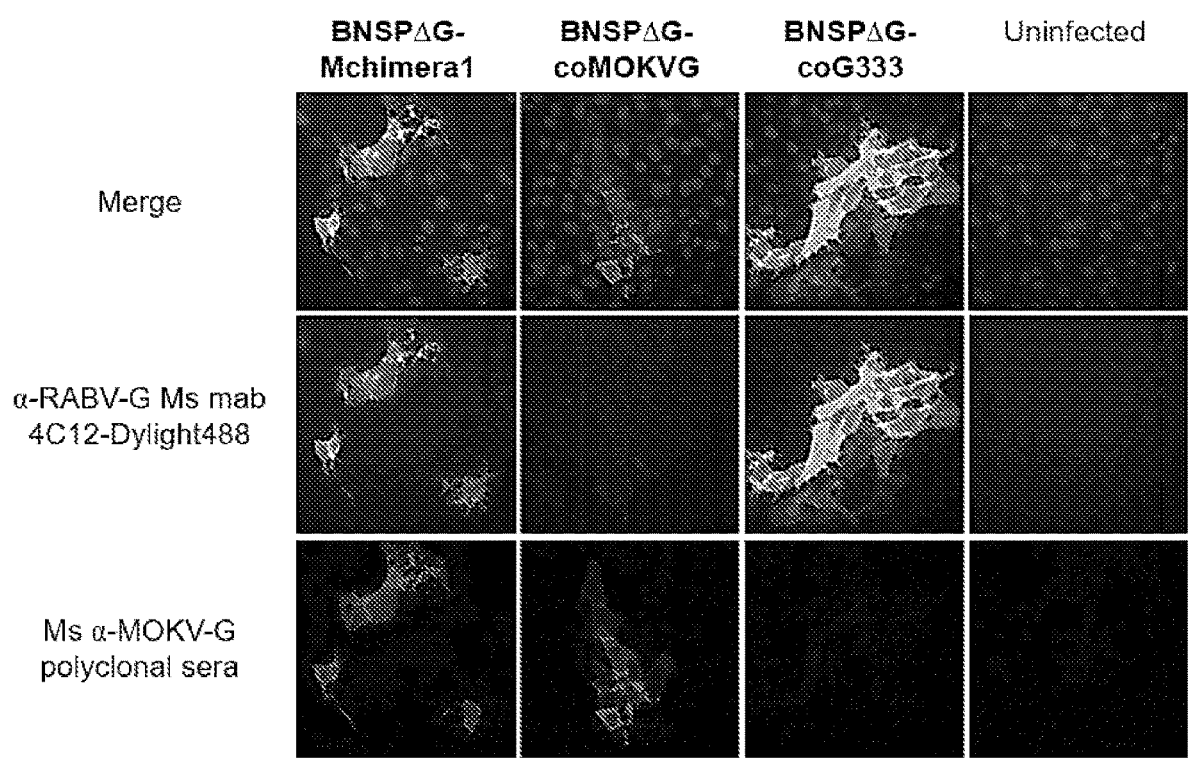
FIG. 6 Immunofluorescence confirmation of chimeric G in infected cells showing response in Chimera 1 to both anti-MOKV-G polyclonal sera and anti-RABV-G monoclonal serum.

FIG. 6. IF data confirms chimeric G cross-reactivity in infected cells. Vero cells are infected with BNSP vectors containing either Chimera 1, MOKV-G, or RABV-G. Following this, the cells are stained with either anti-RABV-G monoclonal antibodies or anti-MOKV-G polyclonal sera. When exposed to anti-RABV-G monoclonal antibodies, the cells containing Chimera 1 and RABV-G react, while cells containing MOKV-G do not. When exposed to anti-MOKV-G polyclonal sera, cells containing Chimera 1 and MOKV-G react, while cells containing RABV-G do not. Uninfected cells act as a control and express no immunofluorescence. The positive staining of clusters of cells demonstrates that the chimeric G is a functional glycoprotein, facilitating viral spread from cell to cell in a live infection. Such functionality enables this vaccine to be produced in the same manner that RABV vaccines are currently produced (viral growth in cell culture).

Figure 8A:
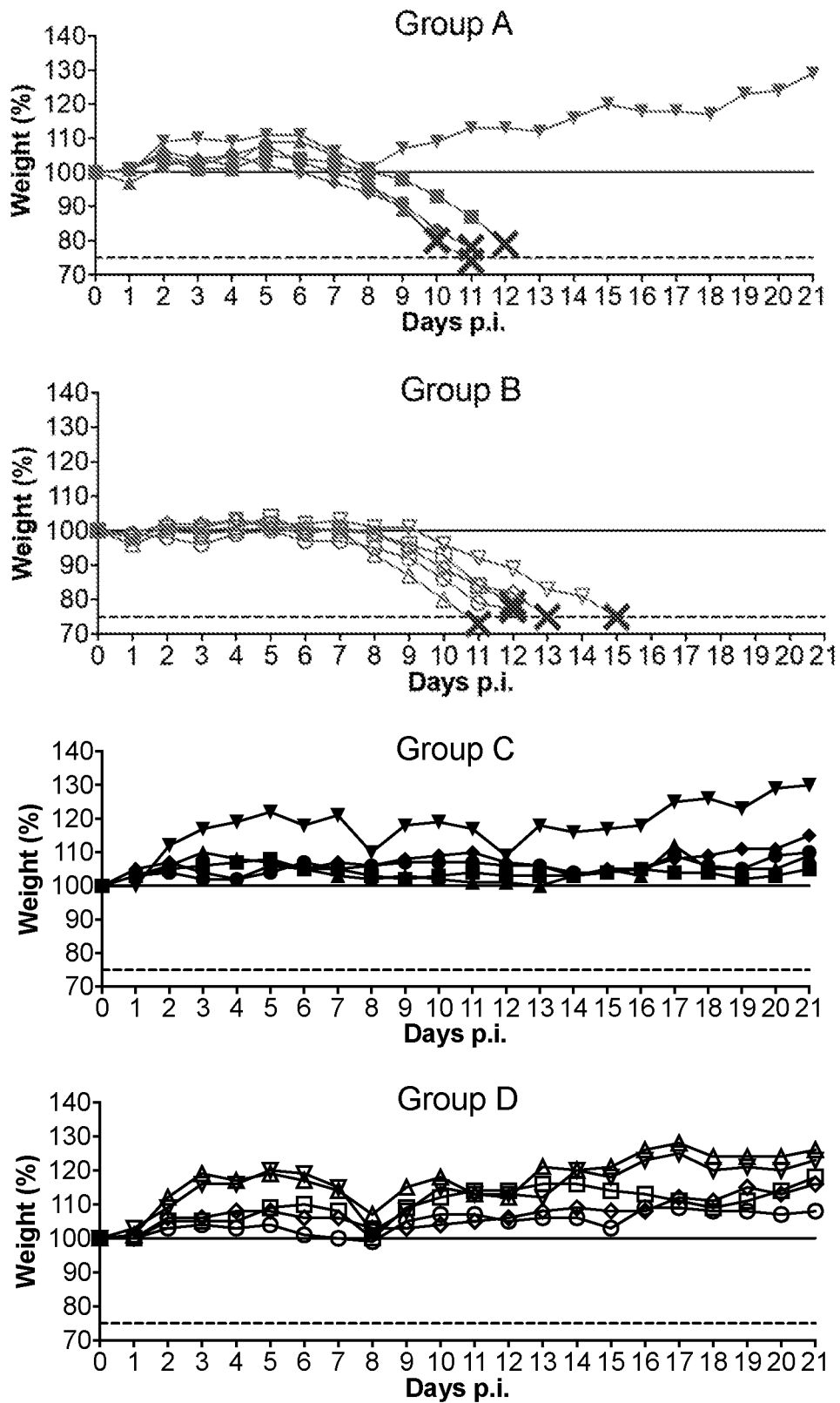

As detailed in FIGS. 8A, 8B, and 8C, the chimeric G vaccine protected mice against disease in a challenge model. Four groups of ten mice were either vaccinated with chimeric G vaccine (BNSPΔG-Chimeral) or mock vaccinated (FIG. 8C). In this particular embodiment, the vaccine was administered in a BPL-inactivated (non-infectious) form, with 10 µg given intramuscularly on days 0, 7, and 28. Then, five mice in each of the four groups were challenged with $5 \times 10^5$ focus forming units (ffu) of recombinant RABV (SPBN) or MOKV (BNSPΔG-coMOKVG) on day 56. FIG. 8B depicts the immunization and challenge schedule.

As seen in FIG. 8A, all mice in groups A (SPBN challenge) and B (BNSPΔG-coMOKVG), which were mock vaccinated, succumbed to disease by day 15 post-challenge, except one mouse in Group A. Mice exhibited neurological symptoms (paralysis, imbalance) and general symptoms of illness (ruffled fur, hunched backs, lethargy, weight loss) and were euthanized when mice lost 25% of their original weight or symptoms became severe. All mice immunized with BNSPΔG-chimera1 and challenged with either SPBN (Group C) or BNSPΔG-coMOKVG (Group D) survived with neither weight less nor disease symptoms. These results demonstrate the in vivo efficacy of the chimeric G vaccine in protecting against two diverse lyssaviruses.

Figure 9A:
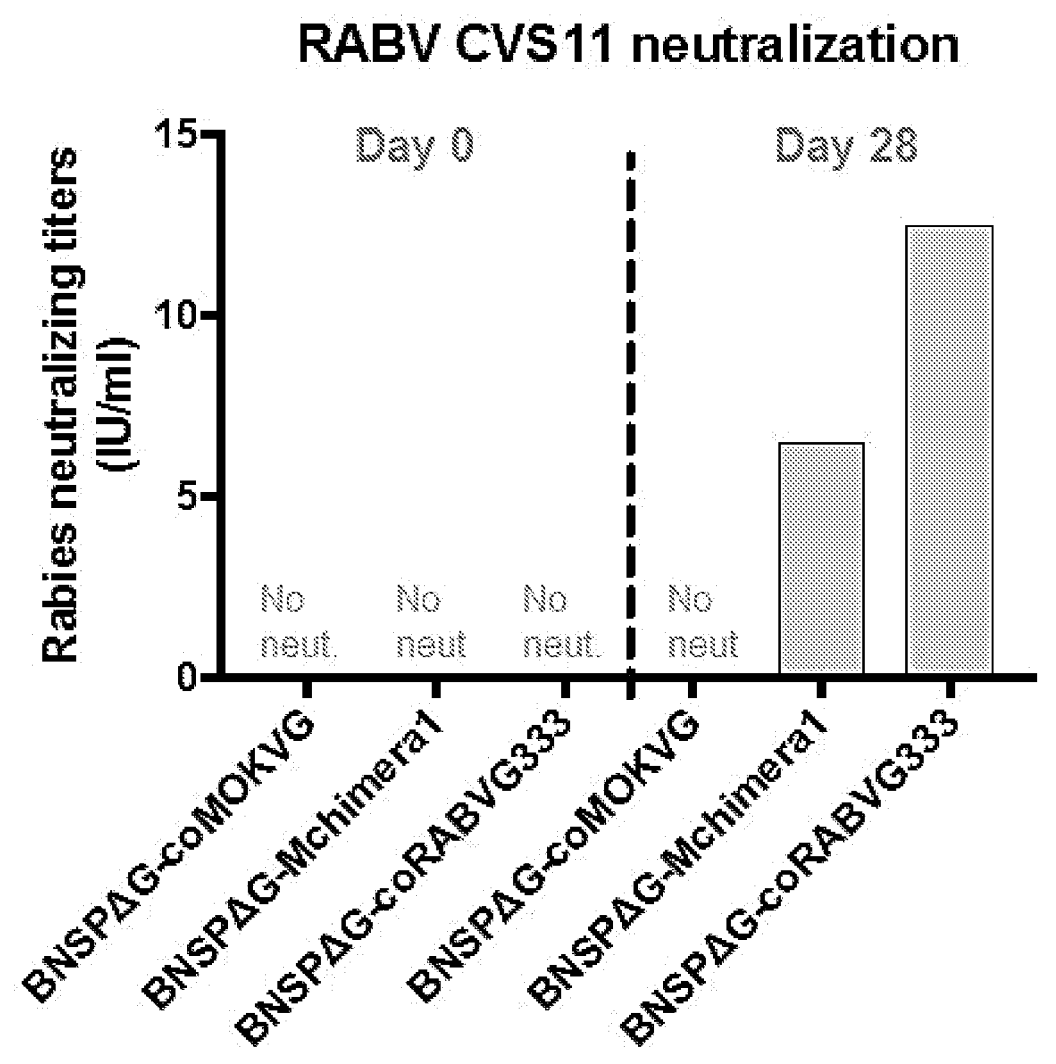
Figure 9B:
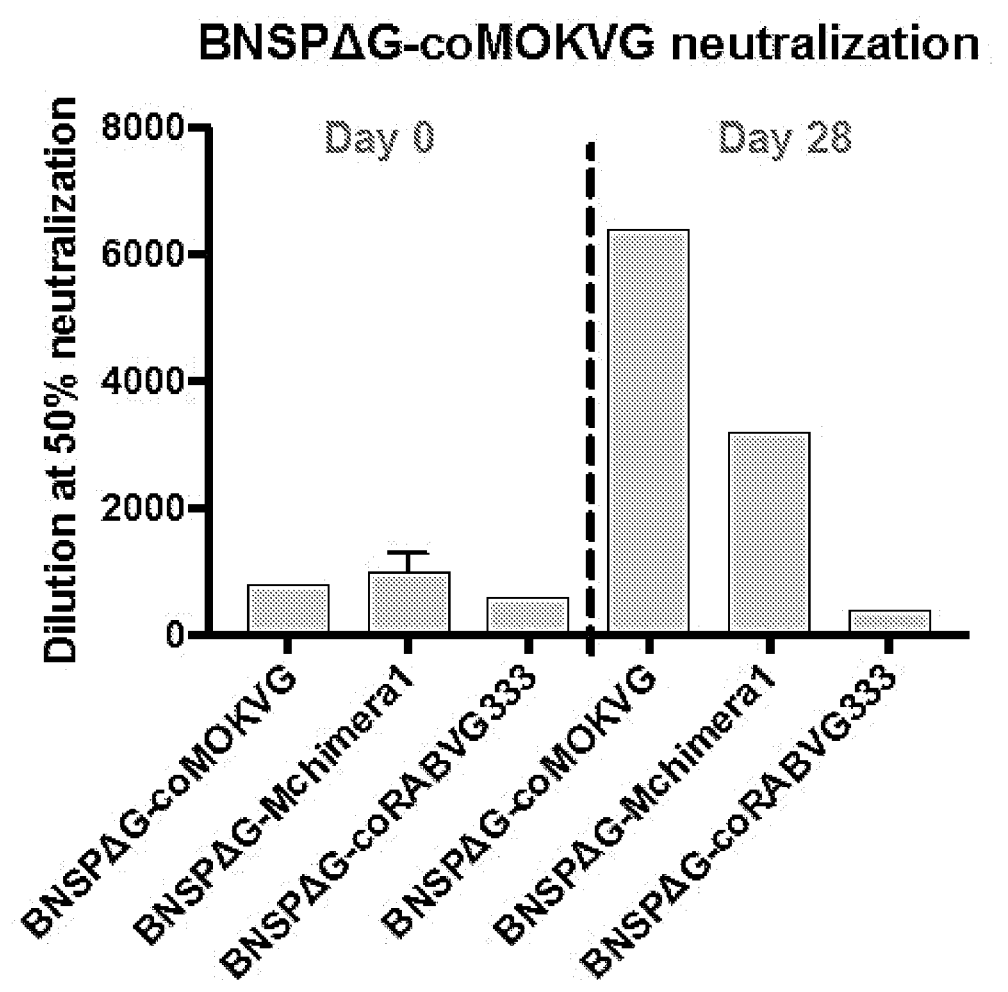

Furthermore, FIG. 9 demonstrates that sera from mice immunized with BNSPΔG-chimera1 can neutralize both RABV G and MOKV G. Three groups of mice were immunized with 10 μg of inactivated (non-infectious) vaccine given intramuscularly on days 0, 7, and 28. One group received BNSPΔG-coMOKVG (containing only a MOKVG G), one group received BNSPΔG-coRABVG333 (containing only a RABV G), and one group received BNSPΔG-chimera1 (containing a RABV/MOKV chimeric G). Sera were collected from mice at numerous timepoints throughout the experiment to examine for reactivity against RABV G or MOKV G. Sera were tested in two in vitro assays: the rapid fluorescent foci inhibition test (RFFIT), which is a standard assay to test for RABV-neutralizing antibodies in sera, and a similar assay using vesicular stomatitis virus pseudotyped with MOKVG. Smith J. S., Yager P. A., Baer G. M. A rapid reproducible test for determining rabies neutralizing antibody. Bull. World Health Organ. 1973; 48:535-541; Moeschler, Sarah, et al. "Quantification of lyssavirus-neutralizing antibodies using vesicular stomatitis virus pseudotype particles." Viruses 8.9 (2016): 254. When sera were compared between days 0 and 28, mice receiving BNSPΔG-coRABVG333 or BNSPΔG-chimera1 generated neutralizing antibodies against RABV. Mice receiving BNSPΔG-coMOKVG or BNSPΔG-chimera1 generated neutralizing antibodies against MOKVG. Only mice immunized with the chimeric G vaccine had sera which could neutralize both. The presence of virus-neutralizing antibodies in serum is a critical indicator that a vaccine will confer protection against a lyssavirus infection.

In a preferred embodiment, the present invention is a chimeric lyssavirus G comprising components of a first lyssavirus G and of a second lyssavirus Gs within a clip region, a core region, a flap region, and a TM and cytoplasmic domain. Most preferably, the first and second lyssaviruses are from different phylogroups.

In a preferred embodiment, the clip, flap, TM and cytoplasmic domain of the chimera come from a RABV G, while the core comes from a MOKV G.

In another preferred embodiment, the clip and flap of the chimera come from a MOKV G, while the core, TM and cytoplasmic domain come from a RABV G.

In one embodiment, a vaccine vector comprising a protein having a chimeric G comprising a structure having a clip, flap, TM, cytoplasmic domain and a core, where the clip, flap, TM and cytoplasmic domain of the chimera come from a RABV G, while the core comes from a MOKV G; and wherein the chimeric G is inserted via standard molecular cloning into the BNSPΔG vector between N and P.

In another embodiment, the chimeric G comprising a structure where the clip and flap of the chimera come from a MOKV G, while the core, TM and cytoplasmic domain come from a RABV G is inserted via standard molecular cloning into the BNSPΔG vector between N and P. In a further embodiment, the chimeric G can be inserted via standard molecular cloning into the BNSPΔG vector before the N, or between the N and P, between the P and M, between the M and L, or after the L.

In a preferred embodiment, the chimeric G of either configuration, when inserted into the BNSPΔG vaccine vector, is recovered in cells using a reverse genetics method, collected from cell culture supernatant, concentrated, purified, inactivated, and provided in a vaccine. Those of skill in the art will recognize other methods of inactivation and purification necessary to allow for intramuscular injection or for other administration protocols.

The embodiments herein, define that the chimeric G, when used in a vaccine, is more effective than standard vaccines and displays cross-reactivity where prior vaccines do not. Chimera 1 inside BNSPΔG is able to successfully infect, replicate within, and bud from cells, bind polyclonal sera that is generated against MOKV G, which otherwise does not cross-react with RABV G, and binds a monoclonal antibody specific to RABV G. (FIG. 6). As such, the ability to generate antibodies against multiple forms of lyssavirus provides a more robust a diverse response that can be used as a method for broadly vaccinating against lyssaviruses, and not simply against certain viruses in the Phylogroup I, as in present vaccines and therapeutics.

In a preferred embodiment, a vaccine comprises a first chimeric G, comprising components of RABV within the clip, flap, TM, and cytoplasmic domain and MOKV within the core; and a second chimeric G comprising MOKV within the clip, flap, TM and cytoplasmic domain, and RABV within the core; wherein said chimeric G's are inserted into a BNSPΔG vector between N and P and prepared in vaccine form (including concentrated, purification, and inactivation).

The invention provides a method of treatment of rabies virus infections comprising the use of a chimeric G containing components of both RABV and MOKV Gs within a clip region, a core region, a flap region, and a TM and cytoplasmic domain, inserted into a BNSPΔG vector between N and P and prepared in vaccine form (including concentrated, purification, and inactivation). The vaccine would be preferably administered through intramuscular administration using a needle, which is the standard method for administrating rabies vaccines. Other suitable administration protocols include intradermal, inhalation, buccal, sublingual, oral, and other forms as known to those of ordinary skill in the art. Those of ordinary skill in the art further recognize how to formulate a vaccine, using appropriate excipients to allow for administration in a preferred dosage form.

In one preferred embodiment, the method of treatment described above would include a dosing regimen of 3 doses of the vaccine over 4 weeks. For example a dosing regimen at 0, 7, and 28 days. This method is intended for pre-exposure treatment and, like standard lyssavirus vaccines, would be used for those at high risk of infection, including those who occupy or frequently travel to areas where canine rabies is endemic.

In another preferred embodiment, the method of treatment described above would include a dosing regimen of between 1 and 5 doses of the vaccine administered over 4 weeks. This method is intended for post-exposure treatment and, like standard lyssavirus vaccines, would be administered to anyone with a known or suspected exposure to confer active immunity.

Presently, those of skill in the art will recognize that there are clinical trials evaluating whether standard rabies vaccines can be administered intradermally using less vaccine and fewer inoculations to lower costs in developing countries. Accordingly, pending an approved reduction in dosing schedule, such schedule may be utilized with the vaccine as described herein, as so far non-inferiority has been demonstrated (https://www.ncbi.nlm.nih.gov/pubmed/29874228).

In certain embodiments the chimeric lyssavirus G may comprise a combination of any two of RABV, IRKV, MOKV and LBV Gs within a clip region, core region, flap region, and TM and cytoplasmic domain.

In a certain embodiment, the chimeric lyssavirus G may comprise a combination of any two Gs of the currently known species of lyssaviruses, including RABV, ARAV, KHUV, BBLV, EBLV-2, ABLY, IRKV, EBLV-1, DUVV, MOKV, SHIBV, LBV, WCBV, IKOV, and LLEBV, within a clip region, a core region, a flap region, and a transmembrane and cytoplasmic domain.

In a certain embodiment, multiple chimeric lyssavirus Gs may be combined into a single "cocktail" vaccine for even more broadly encompassing protection against lyssaviruses. The cocktail preferable comprises at least one chimeric G comprising a first and second lyssavirus in the chimeric G, and at least a second Chimeric G comprising at least a third lyssavirus.

A chimeric G, can be administered alone in its nucleic acid form. Furthermore, the BNSPΔG viral vector can also be administered as a vaccine, in its nucleic acid (RNA or DNA) form. This viral vector vaccine strategy would eliminate the need to create viral particles, concentrate, purify, and inactivate the virus. These viral vectors have been shown to generate a sufficient viral response, and thus could be utilized without the added manufacturing requirements of generating the viral particle. Furthermore, there is potentially added safety concerns, as this would eliminate the possibility of a live viral particle that could cause an infection.

In certain embodiments, the vaccine is administered prophylactically to a mammal, either intramuscularly or orally as a live vaccine. For example, a mammal may include canine, feline, bovine, equine, primates, or other mammal species at risk for rabies infection. The ability to prophylactically administer the vaccine confers protection against rabies exposure in areas wherein one of the lyssaviruses is present and there is risk of rabies transmission. By preventing rabies infections, reduction in the overall rabies viral population can be reduced, and thus reduce risk of infection to mammal populations. These vaccines can also be administered post contact with the rabies virus, and when given early after contact, can reduce the rabies infection and prevent formation of the rabies disease.

REFERENCES

1. WHO. Rabies Fact Sheet, 2016.http://www.who.int/mediacentre/factsheets/fs099/ent
2. Botvinkin A D, Poleschuk E M, Kuzmin I V, Borisova T I, Gazaryan S V, Yager P, Rupprecht C E. Novel lyssaviruses isolated from bats in Russia. Emerg Infect Dis. 2003; 9(12):1623-5. doi: 10.3201/eid0912.030374. PubMed PMID: 14720408; PMCID: PMC3034350.
3. Banyard A C, Evans J S, Luo T R, Fooks A R. Lyssaviruses and bats: emergence and zoonotic threat. Viruses. 2014; 6(8):2974-90. doi: 10.3390/v6082974. PubMed PMID: 25093425; PMCID: PMC4147683.
4. Hanlon C A, Kuzmin I V, Blanton J D, Weldon W C, Manangan J S, Rupprecht C E. Efficacy of rabies biologics against new lyssaviruses from Eurasia. Virus research. 2005; 111(1):44-54.
5. Wei J C, Huang Y Z, Zhong D K, Kang L, Ishag H, Mao X, Cao R B, Zhou B, Chen P Y. Design and evaluation of a multi-epitope peptide against Japanese encephalitis virus infection in BALB/c mice. Biochem Biophys Res Commun. 2010; 396(4):787-92. doi: 10.1016/j.bbrc.2010.04.133. PubMed PMID: 20457131.
6. Zhou W Y, Shi Y, Wu C, Zhang W J, Mao X H, Guo G, Li H X, Zou Q M. Therapeutic efficacy of a multi-epitope vaccine against *Helicobacter pylori* infection in BALB/c mice model. Vaccine. 2009; 27(36):5013-9. doi: 10.1016/j.vaccine.2009.05.009. PubMed PMID: 19446591.
7. Xu H, Hu C, Gong R, Chen Y, Ren N, Xiao G, Xie Q, Zhang M, Liu Q, Guo A, Chen H. Evaluation of a novel chimeric B cell epitope-based vaccine against mastitis induced by either *Streptococcus agalactiae* or *Staphylococcus aureus* in mice. Clin Vaccine Immunol. 2011; 18(6):893-900. doi: 10.1128/CVI.00066-11. PubMed PMID: 21508165; PMCID: PMC3122606.
8. Evans, J. S., Horton, D. L., Easton, A. J., Fooks, A. R. and Banyard, A. C., 2012. Rabies virus vaccines: is there a need for a pan-lyssavirus vaccine?. Vaccine, 30(52), pp. 7447-7454.
9. McGettigan J P, Pomerantz R J, Siler C A, McKenna P M, Foley H D, Dietzschold B, Schnell M J. Second-generation rabies virus-based vaccine vectors expressing human immunodeficiency virus type 1 gag have greatly reduced pathogenicity but are highly immunogenic. Journal of virology. 2003; 77(1):237-44. Epub 2002/12/13. PubMed PMID: 12477829; PMCID: PMC140592.
10. Genz B, Nolden T, Negatsch A, Teifke J P, Conzelmann K K, Finke S. Chimeric rabies viruses for trans-species comparison of lyssavirus glycoprotein ectodomain functions in virus replication and pathogenesis. Berl Munch Tierarztl Wochenschr. 2012; 125(5-6):219-27. PubMed PMID: 22712419.
11. Mebatsion T, Schnell M J, Conzelmann K K. Mokola virus glycoprotein and chimeric proteins can replace rabies virus glycoprotein in the rescue of infectious defective rabies virus particles. Journal of virology. 1995; 69(3):1444-51. PubMed PMID: 7853476; PMCID: PMC188731.
12. Jallet C, Jacob Y, Bahloul C, Drings A, Desmezieres E, Tordo N, Perrin P. Chimeric lyssavirus glycoproteins with increased immunological potential. Journal of virology. 1999; 73(1):225-33. PubMed PMID:9847325; PMCID: PMC103826.
13. Bahloul C, Jacob Y, Tordo N, Perrin P. DNA-based immunization for exploring the enlargement of immunological cross-reactivity against the lyssaviruses. Vaccine. 1998; 16(4):417-25. PubMed PMID: 9607065.
14. Roche S, Bressanelli S, Rey F A, Gaudin Y. Crystal structure of the low-pH form of the vesicular stomatitis virus glycoprotein G. Science. 2006; 313(5784):187-91. doi: 10.1126/science.1127683. PubMed PMID: 16840692.
15. Roche S, Rey F A, Gaudin Y, Bressanelli S. Structure of the prefusion form of the vesicular stomatitis virus glycoprotein G. Science. 2007; 315(5813):843-8.
16. Gomme E A, Faul E J, Flomenberg P, McGettigan J P, Schnell M J. Characterization of a single-cycle rabies virus-based vaccine vector. Journal of virology. 2010;

17. McGettigan J P, David F, Figueiredo M D, Minke J, Mebatsion T, Schnell M J. Safety and serological response to a matrix gene-deleted rabies virus-based vaccine vector in dogs. Vaccine. 2014; 32(15):1716-9. doi: 10.1016/j.vaccine.2014.01.043. PubMed PMID: 24508037; PMCID: PMC3966478.
18. Morimoto K, Schnell M J, Pulmanausahakul R, McGettigan J P, Foley H D, Faber M, Hooper D C, Dietzschold B. High level expression of a human rabies virus-neutralizing monoclonal antibody by a rhabdovirus-based vector. J Immunol Methods. 2001; 252(1-2):199-206. PubMed PMID: 11334980.
19. Cenna J, Tan G S, Papaneri A B, Dietzschold B, Schnell M J, McGettigan J P. Immune modulating effect by a phosphoprotein-deleted rabies virus vaccine vector expressing two copies of the rabies virus glycoprotein gene. Vaccine. 2008; 26(50):6405-14. doi: 10.1016/j.vaccine.2008.08.069. PubMed PMID: 18804506; PMCID: PMC2629409.
20. Mebatsion T. Extensive attenuation of rabies virus by simultaneously modifying the dynein light chain binding site in the P protein and replacing Arg333 in the G protein. Journal of virology. 2001; 75(23):11496-502. doi: 10.1128/JVI.75.23.11496-11502.2001. PubMed PMID: 11689631; PMCID: PMC114736.
21. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect. Dis. 2015; 212 Suppl 2:S414-24. doi: 10.1093/infdis/jiv251. PubMed PMID: 26063224; PMCID: PMC4564550.
22. Blaney J E, Marzi A, Willet M, Papaneri A B, Wirblich C, Feldmann F, Holbrook M, Jahrling P, Feldmann H, Schnell M J. Antibody quality and protection from lethal Ebola virus challenge in nonhuman primates immunized with rabies virus based bivalent vaccine. PLoS pathogens. 2013; 9(5):e1003389. doi: 10.1371/journal.ppat.1003389. PubMed PMID: 23737747; PMCID: PMC3667758.
23. Kurup D, Wirblich C, Feldmann H, Marzi A, Schnell M J. Rhabdovirus-based vaccine platforms against henipaviruses. Journal of virology. 2015; 89(1):144-54. doi: 10.1128/JVI.02308-14. PubMed PMID: 25320306; PMCID: PMC4301098.
24. McGettigan J P, Sarma S, Orenstein J M, Pomerantz R J, Schnell M J. Expression and immunogenicity of human immunodeficiency virus type 1 Gag expressed by a replication-competent rhabdovirus-based vaccine vector. Journal of virology. 2001; 75(18):8724-32. Epub 2001/08/17. PubMed PMID: 11507217; PMCID: PMC115117.
25. Johnson N, Cunningham A F, Fooks A R. The immune response to rabies virus infection and vaccination. Vaccine. 2010; 28(23):3896-901. doi: 10.1016/j.vaccine.2010.03.039. PubMed PMID: 20368119.
26. Schnell M J, McGettigan J P, Wirblich C, Papaneri A. The cell biology of rabies virus: using stealth to reach the brain. Nat Rev Microbiol. 2010; 8(1):51-61. doi: 10.1038/nrmicro2260. PubMed PMID: 19946287.
27. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular therapy Methods & clinical development. 2014; 1:14046. doi: 10.1038/mtm.2014.46. PubMed PMID: 26015984; PMCID: PMC4362357.
28. Reardon T R, Murray A J, Turi G F, Wirblich C, Croce K R, Schnell M J, Jessell T M, Losonczy A. Rabies Virus CVS-N2c Strain Enhances Retrograde Synaptic Transfer and Neuronal Viability. Neuron. 2016. doi: 10.1016/j.neuron.2016.01.004. PubMed PMID: 26804990.
29. Papaneri A B, Bernbaum J G, Blaney J E, Jahrling P B, Schnell M J, Johnson R F. Controlled viral glycoprotein expression as a safety feature in a bivalent rabies-ebola vaccine. Virus research. 2015; 197:54-8. doi: 10.1016/j.virusres.2014.11.028. PubMed PMID: 25481284; PMCID: PMC4362543.
30. Papaneri A B, Wirblich C, Marissen W E, Schnell M J. Alanine scanning of the rabies virus glycoprotein antigenic site III using recombinant rabies virus: implication for post-exposure treatment. Vaccine. 2013; 31(49):5897-902. Epub 2013/10/15. doi: 10.1016/j.vaccine.2013.09.038. PubMed PMID: 24120673.

What is claimed is:

1. A chimeric lyssavirus glycoprotein comprising components of both RABV and MOKV glycoproteins within a clip region, a core region, a flap region, and a transmembrane and cytoplasmic domain, wherein the clip region is from a MOKV glycoprotein; wherein the core region is from a RABV glycoprotein; wherein the flap region is from a MOKV glycoprotein; and wherein the transmembrane and cytoplasmic domain are from a RABV glycoprotein.

2. The chimeric glycoprotein of claim 1 wherein the glycoprotein is inserted into a rabies virus vector between the nucleoprotein and the phosphoprotein.

3. The chimeric glycoprotein of claim 2 wherein the glycoprotein inserted into the a rabies vector is inactivated and provided in an immunogenic composition.

4. The chimeric glycoprotein of claim 1, wherein the clip region, a core region, a flap region, and a transmembrane and cytoplasmic domain are defined by starting from the amino terminus of the protein, these domains are comprised of the following amino acid residue ranges: clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain.

5. A method of eliciting an immunogenic response to lyssaviruses comprising intramuscular administration of an immunogenic composition containing inactivated chimeric glycoprotein viruses, wherein said inactivated chimeric glycoprotein viruses comprise components of both RABV and MOKV glycoproteins within a clip region, a core region, a flap region, and a transmembrane and cytoplasmic domain, wherein the clip region is from a MOKV glycoprotein, wherein the core region is from a RABV glycoprotein, wherein the flap region is from a MOKV glycoprotein, and wherein the transmembrane and cytoplasmic domain are from a RABV glycoprotein.

6. The method of claim 5 wherein the immunogenic composition is administered as at least 3 doses over 4 weeks.

7. The method of claim 5 wherein the immunogenic composition is administered as at least 4 doses over 4 weeks.

8. The method of claim 5, wherein the clip region, core region, flap region, transmembrane, and cytoplasmic domain are defined by starting from the amino terminus of the and are comprised of the following amino acid residue ranges: clip, 1 through 40 to 60; core, 40 to 60 through 249 to 281; flap, 249 to 281 through 419 to 459; the transmembrane domain is comprised of amino acids 460 through 480, and the remaining amino acids 481 through 525 comprise the cytoplasmic domain.

9. A nucleic acid encoding a chimeric G, comprising a clip region, core region, flap region, and a transmembrane and cytoplasmic domain of at least two different lyssaviruses, administered to a patient in its nucleic acid form, wherein the clip region is from a MOKV glycoprotein; wherein the core region is from a RABV glycoprotein; wherein the flap region is from a MOKV glycoprotein; and wherein the transmembrane and cytoplasmic domains are from a RABV glycoprotein.

10. A rabies viral vector comprising the nucleic acid of claim 9.

* * * * *